United States Patent [19]

Reid et al.

[11] Patent Number: 5,221,462
[45] Date of Patent: Jun. 22, 1993

[54] METHODS FOR RETARDING COKE FORMATION DURING PYROLYTIC HYDROCARBON PROCESSING

[75] Inventors: Dwight K. Reid, Houston; Daniel E. Fields, The Woodlands, both of Tex.

[73] Assignee: Betz Laboratories, Inc., Trevose, Pa.

[21] Appl. No.: 676,043

[22] Filed: Mar. 27, 1991

[51] Int. Cl.$^5$ ................................................ C10G 9/16
[52] U.S. Cl. ............................. 208/48 AA; 208/48 R; 585/950
[58] Field of Search .................... 585/648, 650, 950; 208/48 AA, 47

[56] References Cited

U.S. PATENT DOCUMENTS

| | | | |
|---|---|---|---|
| 1,847,095 | 3/1932 | Mittasch et al. | 208/48 |
| 2,063,596 | 12/1936 | Feiler | 196/133 |
| 3,342,723 | 9/1967 | Godar | 208/48 |
| 3,531,394 | 9/1970 | Koszman | 208/48 |
| 3,661,820 | 5/1972 | Foreman et al. | 260/22 A |
| 3,687,840 | 8/1972 | Sze et al. | 208/131 |
| 4,105,540 | 8/1978 | Weinland | 208/48 AA |
| 4,378,288 | 3/1983 | Shih et al. | 208/131 |
| 4,511,457 | 4/1985 | Miller et al. | 208/48 AA |
| 4,555,326 | 11/1985 | Reid | 208/48 |
| 4,680,421 | 7/1987 | Forester et al. | 585/648 |
| 4,724,064 | 2/1988 | Reid | 108/48 |
| 4,941,968 | 7/1990 | Reid | 208/48 AA |

FOREIGN PATENT DOCUMENTS

| | | | |
|---|---|---|---|
| 275662 | 8/1928 | United Kingdom | 208/48 |
| 296752 | 9/1928 | United Kingdom | 260/668 |

OTHER PUBLICATIONS

Chemical Abstracts: vol. 83:30687K 1975.
Chemical Abstracts: vol. 87:154474r 1977.
Chemical Abstracts: vol. 95:135651v 1981.
Chemical Abstracts: vol. 92:8645j 1980.

*Primary Examiner*—Helane Myers
*Attorney, Agent, or Firm*—Alexander D. Ricci; Philip H. Von Neida

[57] ABSTRACT

The present disclosure is directed to methods for controlling undesirable coke formation and deposition on structural surfaces which is commonly encountered during the high temperature processing of hydrocarbons. Coke formation can be inhibited by adding an effective amount of a dihydroxybenzene to the system suffering from coke formation.

6 Claims, No Drawings

METHODS FOR RETARDING COKE FORMATION DURING PYROLYTIC HYDROCARBON PROCESSING

FIELD OF THE INVENTION

The present invention is directed towards a method of inhibiting the formation and deposition of coke on surfaces in contact with hydrocarbons. More specifically, the present invention relates to inhibiting the formation and deposition of coke on the surfaces of furnaces during the high temperature pyrolysis of hydrocarbons using certain dihydroxybenzenes.

BACKGROUND OF THE INVENTION

Coke deposition is generally experienced when hydrocarbon liquids and vapors contact the hot metal surfaces of petroleum processing equipment. Due to the complex makeup of the hydrocarbons upon elevated temperatures and contact with hot metal surfaces, it is not entirely understood what changes occur in the hydrocarbons. It is thought that the hydrocarbons undergo various changes through either chemical reactions and/or decomposition of various unstable components of the hydrocarbon. The undesired products in many instances include coke, polymerized products, deposited impurities and the like. Whatever the undesired product that is formed, reduced economies of the process is the result. If these deposits remain unchecked, heat transfer, throughput and overall productivity are detrimentally effected. Moreover, downtime is likely to be encountered due to the necessity of either replacing and/or cleaning of the affected parts of the processing system.

While the formation and type of undesired products are dependent on the hydrocarbon being processed and the conditions of the processing, it may generally be stated that such products can be produced at temperatures as low as 100° F.; but are much more prone to formation as the temperature of the processing system and the metal surfaces thereof in contact with the hydrocarbon increase. At these temperatures, coke formation is likely to be produced regardless of the type of hydrocarbon being charged. The type of coke formed, i.e., amorphous, filamentous or pyrolytic, may vary somewhat; however, the probability of the formation of such is quite high.

Carbon formation also erodes the metal of the system in two ways. The formation of catalytic coke causes the metal catalyst particle to be dislodged. This results in rapid metal loss and ultimately metal failure. The other erosive effect occurs when carbon particles enter the hydrocarbon stream and act as abrasives on the system's tube walls.

As indicated in U.S. Pat. Nos. 3,531,394 and 4,105,540 which are herein incorporated by reference, coke formation and deposition are common problems in ethylene plants which operate at temperatures where the metal surfaces in contact with the hydrocarbon are sometimes at 1600° F. and above. The problem is prevalent in the cracking furnace coils as well as in the transfer line exchangers (TLEs) where pyrolytic type coke formation and deposition is commonly encountered. Ethylene plants, originally produced simple olefins such as ethylene, propylene, butenes and butadiene from a feed of ethane, propane, butanes and mixtures thereof. Later developments in the area of technology however, have led to the cracking of heavier feedstocks, because of their availability, to produce aromatics and pyrolysis gasoline as well as light olefins. Feed stocks now include light naphtha, heavy naphtha and gas oil. According to the thermal cracking processes utilized in olefin plants, the feedstocks are cracked generally in the presence of steam in tubular pyrolysis furnaces. The feedstock is preheated, diluted with steam and the mixture heated in the pyrolysis furnace to about 1500° F. and above, most often in the range of 1500° F., to 1650° F. The effluent from the furnace is rapidly quenched by direct means or in exchangers which are used to generate high pressure steam at 400 to 800 psig for process use. This rapid quench reduces the loss of olefins by minimizing secondary reactions. The cooled gas then passes to the prefractionator where it is cooled by circulating oil streams to remove the fuel oil fraction. In some designs, the gas leaving the quench exchanger is further cooled with oil before entering the prefractionator. In either case, the heat picked up by the circulating oil stream is used both to generate steam and to heat other process streams. The mixture of gas and steam leaving the prefractionator is further cooled in order to condense the steam and most of the gasoline product in order to provide reflux for the prefractionator. Either a direct water quench or heat exchangers are used for this cooling duty.

After cooling, cracked gas at, or close to atmospheric pressure, is compressed in a multistage compression system to much higher pressures. There are usually four or five stages of compression with interstage cooling and condensate separation between stages. Most plants have hydrocarbon condensate stripping facilities. Condensate from the interstage knockout drum is fed to a stripper where the $C_2$ and lighter hydrocarbons are separated. The heavier hydrocarbons are fed to the depropanizer.

GENERAL DESCRIPTION OF THE INVENTION

The present invention pertains to a method for inhibiting the formation and deposition of pyrolytic coke on the heated metal surfaces in contact with a hydrocarbon feedstock which is undergoing pyrolytic processing to produce lower hydrocarbon fractions and said metal surfaces having a temperature of about 1600° F. or above, which method comprises adding to said hydrocarbon feedstock being processed a coke inhibiting amount of a dihydroxybenzene compound.

While the invention is applicable to any system where coke is produced, this invention is surprisingly effective during the high temperature pyrolysis and cracking of a hydrocarbon feedstock.

DESCRIPTION OF THE RELATED ART

French Patent No. 2,202,930 (Chem. Abstracts Vol. 83:30687k) is directed to tubular furnace cracking of hydrocarbons where molten oxides or salts of Group III IV or VIII metals (e.g. molten lead containing a mixture of $K_3VO_4$, $SiO_2$ and $NiO$) are added to a pretested charge of, for example, naphtha steam at 932° F. This treatment is stated as having reduced deposit and coke formation in the cracking section of the furnace.

Starshov et al., Izv. Vyssh. Uchebn. Zaved Neft Gaz, 1977 (Chem. Abst. 87:154474r) describes the pyrolysis of hydrocarbons in the presence of aqueous solutions of boric acid. Carbon deposits were minimized by this process.

Nokonov et al., U.S.S.R. No. 834,107, 1981; (Chem. Abst. 95:13565v) describes the pyrolytic production of olefins with peroxides present in a reactor, the internal surfaces of which have been pretreated with an aqueous alcoholic solution of boric acid. Coke formation is not mentioned in this patent since the function of boric acid is to coat the inner surface of the reactor and thus decrease the scavenging of peroxide radicals by the reactor surface.

Starshov et al., Neftekhimiya 1979 (Chem. Abst. 92:8645j) describes the effect of certain elements including boron on coke formation during the pyrolysis of hydrocarbons to produce olefins.

U.S. Pat. No. 3,531,394 (Koszman) teaches the inhibition of carbon formation in the thermal cracking of petroleum fractions. His process teaches the use of bismuth and phosphorous containing compounds to reduce carbon formation.

U.S. Pat. No. 3,661,820 (Foreman et al.) teaches a composition that is used as a coating for steel surfaces. This composition will prevent carburization in gas carburizing, pack carburizing and carbonitriding mediums. The composition taught is a boron compound selected from boric acid, boric oxide and borax; water soluble organic resin; carrier fluid of water and thickening and drying agents.

U.S. Pat. No. 2,063,596 (Feiler) teaches a method of treating the metal of a system processing hydrocarbons at high temperatures. This patent discloses the suppression of the deposition of carbon on the metal surfaces of a hydrocarbon process using the metals tin, lead, molybdenum, tungsten and chromium to coat the metal surfaces. This patent conjectures as to the use of a metalloid of boron as a treating agent.

Great Britain 296,752 teaches a method of preventing deposition of coke or soot on metal surfaces in contact with hydrocarbons at high temperatures. The metals are treated directly with metalloids of boron, arsenic, bismuth, antimony, phosphorous or selenium.

Great Britain 275,662 teaches a process for preventing the formation of carbon monoxide in a hydrocarbon cracking operation. This process involves coating the metal surfaces that contact the hydrocarbon with metalloids of boron, arsenic, antimony, silicon, bismuth, phosphorous or selenium.

U.S. Pat. No. 1,847,095 (Mittasch et al.) teaches a process for preventing the formation and deposition of carbon and soot in hydrocarbon processes operating at elevated temperatures. This process consists of adding to the hydrocarbon stream hydrides of metalloids selected from the group of boron, arsenic, antimony, bismuth, phosphorous, selenium and silicon.

U.S. Pat. No. 3,687,840 (Sze et al.) teaches a method of stopping plugs in a delayed coker unit that result from the formation and deposition of coke. This process employs sulfur and sulfur compounds a the inhibiting agents.

U.S. Pat. No. 4,555,326 (Reid) teaches a method of inhibiting the formation and deposition of filamentous coke in hydrocarbon processing systems operating at high temperatures. The metal that contacts the hydrocarbon fluid is first treated ("boronized") by contacting it with boron, boron oxide compounds or metal borides.

U.S. Pat. No. 4,729,064 (Reid) teaches a method of inhibiting the formation and deposition of filamentous coke on metal surfaces in contact with a hydrocarbon fluid at high temperatures. Boron oxide compounds, metal borides and boric acid which is substantially free of water are the inhibiting agents.

U.S. Pat. No. 4,680,421 (Forester et al.) discloses a method of inhibiting the formation and deposition of pyrolytic coke on the heated metal surfaces of a pyrolysis furnace. This method employs an ammonium borate compound to inhibit the deposition on the 1600° F. and higher temperature metal surfaces.

U.S. Pat. No. 3,342,723, Godar, teaches a method of inhibiting the formation of coke-like deposits in oil refining apparatus operating in a range from 200° to 800° F. Representative antifouling agents include catechol, 4-tert-butyl catechol and orthophenylene diamine. Hydroquinone proved to be ineffective at inhibiting the coke-like deposits.

DETAILED DESCRIPTION OF THE INVENTION

The present invention pertains to a method for inhibiting the formation and deposition of pyrolytic coke on the heated metal surfaces in contact with a hydrocarbon feedstock which is undergoing pyrolytic processing to produce lower hydrocarbon fractions and said metal surfaces having a temperature of about 1600° F. or higher, which improvement comprises the method of adding to said hydrocarbon feedstock being pyrolytically processed a coke inhibiting amount of a dihydroxybenzene compound.

While the method is applicable to any system where coke is formed, it is particularly effective at inhibiting the formation and deposition of coke on the surfaces of furnaces during the high temperature pyrolysis and cracking of hydrocarbons using certain dihydroxybenzene compounds.

The methods of this invention are adapted to inhibit the formation and deposition of coke on metallic surfaces in contact with a hydrocarbon in either liquid or gaseous form. The metallic surfaces reach temperature of 1400° F. and above, up to 1500°-2050° F. These temperatures are commonly encountered in olefin plants where hydrocarbon feedstocks containing ethane, propane, butanes, light naphtha, heavy naphtha, gas oil, and mixtures of the same are cracked to produce lower and/or olefinic hydrocarbon fractions. In these systems, the components of the pyrolytic furnace as well as the ancillary parts are composed of ferrous metal. Iron, as well as iron alloys such as low and high carbon steel, and nickel-chromium-iron alloys are customarily used for the production of hydrocarbon processing equipment such as furnaces, transmission lines, reactors, heat exchangers, fractionators and the like.

It has been found that during the high temperature pyrolytic processing of hydrocarbons, coke will form and deposit on the stainless steel surfaces of the system. This formation and deposition on the stainless steel surfaces can be significantly reduced in accord with the test herein by use of a dihydroxybenzene compound.

Accordingly, it is to be expected that coke formation will also be reduced on iron, chromium and nickel based metallurgical surfaces in contact with pyrolysis products in high temperature pyrolytic furnaces.

The dihydroxybenzene compounds are effective when formulated in water with a co-solvent such as butyl carbitol or ethylene glycol. The compound may be added directly to the hydrocarbon feedstock or charge before an/or during the pyrolytic processing, or the treatment composition may be mixed with steam carried to the cracking zone in accordance with conventional cracking techniques.

The treatment dosages for the dihydroxybenzene compounds are dependent upon the severity of the coking problem, location of such problem, and the amount of active compound in the formulated product. For this reason, the success of the treatment is totally dependent upon the use of a sufficient amount of the treatment composition thereby to effectively inhibit coke formation and deposition.

Preferably, the total amount of dihydroxybenzene compound added is from about 1 ppm to about 2500 ppm per million parts of feedstock. More preferably, from about 20 ppm to about 500 ppm per million parts of feedstock.

The preferred dihydroxybenzene is hydroquinone, however, the present inventors anticipate that resorcinol, catechol, 1,2-naphthoquinone, 1,4-naphthoquinone and 4-tert-butylresorcinol will also be effective in the instant invention.

The invention will now be further described with reference to a number of specific examples which are to be regarded solely as illustrative, and not as restricting the scope of the invention.

EXAMPLES

In order to establish the efficacy of the invention, various tests were conducted using a propane feedstock with dilution steam added to enhance cracking. The apparatus and procedure used for the testing were as follows:

APPARATUS

The High Temperature Fouling Apparatus (HTFA) consists of five subsections which together simulate the pyrolysis of gaseous hydrocarbons to make the light olefinic end products and the undesirable by-product, coke, that is formed on the heated metal surfaces during the pyrolysis reaction.

The feed preheat section is built of 316 stainless steel tubing and fittings and allows the mixing of nitrogen or oxygen containing gas with steam during the start up and shut down of the HFTA and the propane with steam during the actual test. Steam is supplied at 40 psig by a steam generator and nitrogen, oxygen containing gas, or propane is fed from compressed gas cylinders. The gases and steam are heated to about 300° F. at which point small amounts of water (blank test) or candidate material is slowly injected into the stream by a syringe pump. The gases/candidate material are further preheated to about 500° F. before flowing through a 13 foot long coiled 316 SS tube inside an electrically heated furnace. The gases are heated at a furnace temperature of approximately 1880° F. and exit the furnace at 1150°-1450° F.

Following the furnace tube, the gases travel through the coker rod assembly. This consists of a 316 SS rod which is electrically heated to 1500° F. while the gases flow around the heated rod inside a 316 SS shell. The rod is electrically heated through a silicon controlled rectifier (SCR), then through the 4 to 1 stepdown transformers in series to achieve low voltage (3–4 volts) and high amperage (200 amps) heating of the rod. A temperature controller is used to achieve power control through the SCR to obtain a 1500° F. rod temperature.

Upon exiting the coker rod, the gases pass through a condenser coil and then through three knock-out flasks in ice baths to remove the water (steam) from the product gases. The small amount of remaining entrained water vapor in the gases is removed by passing through drierite granules.

The specific gravity of the product gas is determined in a gas densitometer and the gases are analyzed using gas chromotography to determine yields. The remaining gases are vented through a safety hood exhaust.

TEST PROCEDURE

The furnace was turned on and the temperature thereof was stabilized at 1300° F. while feeding nitrogen and steam. The coker rod was heated to 1500° F. The nitrogen was replaced with oxygen containing gas (air) and furnace temperatures were then slowly increased to 1500° F. over a period of ten minutes. Then the air was replaced with nitrogen and the coke inhibitor water (blank), as the case may be, was injected into the mixed gas or steam line at about 300° F. gas temperature while the furnace temperature was slowly raised to 1880° F. over 20–25 minutes.

Then the nitrogen feed was gradually switched to propane feed over about 5 minutes. The temperature of the furnace dropped due to the propane cracking reaction and was allowed to increase to the maximum attainable furnace temperature (1880° F. or less) over approximately a 30 minute period. The product gases were analyzed by gas chromatography and the temperatures, flow-rates, pressures and product gas gravity recorded every 35 minutes during the 160 minute test on propane/steam feed. Gases exit the furnace tube at about 1150° F.–1450° F. and exit the coker smell at about 975° F.–1000° F. temperatures.

During a normal 160 minute run, approximately 3200–3300 grams of propane were fed and 1000–2000 grams of steam fed (determined from the condensate collected) for hydrocarbon to steam rates of about 1.6:1 to 3.2:1.

Following shutdown and cooling, the furnace tube and coker shell were cleaned and the coke collected and weighed. The collected coke was then burned in air at 1400° F. for one hour and the residue remaining weighed and termed gray matter (corrosion products from furnace tube).

Table I reports the results of the above test by indicating the amount of coke formed for various antifoulants. A high percentage coke reduction value is indicative of effective treatment.

TABLE I

High Temperature Fouling Apparatus (HFTA)
Results for coke inhibiting compounds
1300°–1500° F. Furnace Steam/Air Decoke
1500°–1870° F. Furnace Propane (0.5 SCFM)/Steam/
Antifoulant for 2.67 Hrs.

| Antifoulant (ppm, Metal) | Steam (ml/min) | Coke Formed (Grams) | Gray Formed[1] (Grams) | Predicted[2] Coke, Grams | % Coke[3] Reduction |
|---|---|---|---|---|---|
| 10% HQ/EG (176) | 10.64 | 0.57 | 5.53 | 0.60 | 4 |
| 10% HQ/EG (168) | 10.91 | 0.06 | 5.46 | 0.58 | 90 |

TABLE I-continued

High Temperature Fouling Apparatus (HFTA)
Results for coke inhibiting compounds
1300°-1500° F. Furnace Steam/Air Decoke
1500°-1870° F. Furnace Propane (0.5 SCFM)/Steam/
Antifoulant for 2.67 Hrs.

| Antifoulant (ppm, Metal) | Steam (ml/min) | Coke Formed (Grams) | Gray Formed[1] (Grams) | Predicted[2] Coke, Grams | % Coke[3] Reduction |
|---|---|---|---|---|---|
| 10% HQ/EG (173) | 12.88 | 0.44 | 0.75 | 0.49 | 11 |
| 30% HQ/EG (561) | 11.62 | 0.30 | 0.53 | 0.55 | 45 |
| 20% HQ/EG (229) | 14.27 | 0.22 | 0.18 | 0.45 | 51 |
| 20% HQ/EG (261) | 9.56 | 0.31 | 0.26 | 0.67 | 54 |
| 10% 1-NAPH/EG (170) | 13.66 | 0.78 | 1.28 | 0.47 | −67 |
| 10% t-BUT HQ/EG (193) | 9.50 | 0.81 | 3.31 | 0.67 | −21 |
| 10% 1,5-DHN/EG (171) | 13.63 | 1.05 | 5.35 | 0.47 | −125 |

[1] Gray is the corrosion products removed from furnace tube/coker shell that remain after the total coke collected is burned at 1400° F. in air.
[2] Predicted coke = 6.37/condensate rate (ml/min)
[3] % Coke Reduction = [1 − coke formed/predicted coke] * 100
HQ = Hydroquinone
EG = Ethylene Glycol
EA = Ethanolamine
1-NAPH = 1-Naphthol
t-BUT HQ = Tertbutyl Hydroquinone
1,5-DHN = 1,5-Dihydroxynaphthalene

DISCUSSION

The six HFTA runs treated with HQ in solvents exhibited an average coke reduction of 43% +/−31%. Employing the Mann-Whitney statistical comparison test, the treated runs were greater than the untreated runs at a 95.2% confidence level.

Accordingly, from the above, it is clear that dihydroxybenzene compounds, particularly hydroquinone, are effective as coke retarding treatments under the simulated pyrolysis conditions above noted.

While this invention has been described with respect to particular embodiments thereof, it is apparent that numerous other forms and modifications of this invention will be obvious to those skilled in the art.

Having thus described the invention, we claim:

1. A method of inhibiting the formation and deposition of pyrolytic coke on the heated metal surfaces in contact with a hydrocarbon feedstock which is undergoing pyrolytic processing to produce lower hydrocarbon fractions and said metal surfaces having a temperature of about 1400° F. or higher, consisting essentially of adding to said hydrocarbon feedstock being pyrolytically processed a coke inhibiting amount of hydroquinone.

2. A method as claimed in claim 1 wherein the hydroquinone compound is contained in an ethylene glycol water co-solvent carrier.

3. A method as claimed in claim 1 wherein pyrolysis furnace.

4. A method as claimed in claim 1 wherein delayed coker system.

5. A method as claimed in claim 1 wherein said metallic surfaces are ferrous metal surfaces.

6. A method as claimed in claim 1 wherein said hydrocarbon comprises ethane, propane, butane, naphtha, gas oil, or mixtures thereof.

* * * * *